United States Patent [19]

Covey et al.

[11] Patent Number: 5,134,133

[45] Date of Patent: Jul. 28, 1992

[54] OXIME PHOSPHATE PESTICIDAL COMPOUNDS, COMPOSITIONS AND METHODS

[75] Inventors: Rupert A. Covey, Bethany; Patricia J. Forbes, Waterbury; Richard R. Regis, Torrington; Richard C. Moore, Wallingford; Kevin J. Donovan, Cheshire; Paul T. McDonald, Middlebury, all of Conn.

[73] Assignee: Uniroyal Chemical Company, Inc., Middlebury, Conn.

[21] Appl. No.: 768,148

[22] Filed: Sep. 30, 1991

[51] Int. Cl.$^5$ .................. C07D 257/04; A01N 43/713; A01N 57/16; C07F 9/141

[52] U.S. Cl. ..................................... 514/92; 548/112; 424/405

[58] Field of Search ............. 574/79, 80, 92; 548/112, 113, 251, 252, 254; 424/405

[56] References Cited

U.S. PATENT DOCUMENTS

| | | | |
|---|---|---|---|
| 3,780,053 | 12/1973 | Miesel | 548/112 |
| 4,036,987 | 7/1977 | Thompson et al. | 424/325 |
| 4,211,703 | 7/1980 | Berger | 548/112 |
| 4,327,090 | 4/1982 | Buerstinghaus | 424/203 |
| 4,330,536 | 5/1982 | Pissiotas | 424/200 |
| 4,399,444 | 7/1982 | D'Silva | 424/202 |
| 4,424,215 | 1/1984 | Buerstinghaus | 424/210 |
| 4,535,077 | 8/1985 | Fahmy | 514/143 |
| 4,562,259 | 12/1985 | Theobald et al. | 548/112 |
| 4,568,668 | 2/1986 | Buerstinghaus | 514/99 |
| 4,612,306 | 9/1986 | Buerstinghaus | 514/112 |
| 4,618,365 | 10/1986 | Covey | 71/92 |
| 4,670,425 | 6/1987 | Buerstinghaus | 514/112 |
| 4,839,349 | 6/1989 | Covey | 514/92 |
| 5,049,554 | 9/1991 | Covey et al. | 514/92 |

Primary Examiner—Thurman K. Page
Assistant Examiner—Neil S. Levy
Attorney, Agent, or Firm—Glenn E. Karta

[57] ABSTRACT

A class of compounds useful for providing long-term control of pests, such as insects, nematodes and acarids, having the structural formula:

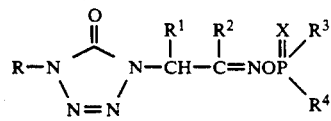

where R is lower alkyl, phenyl, substituted phenyl, naphthyl or substituted napthyl; $R^1$ is hydrogen or $C_1$-$C_6$ alkyl; $R^2$ is $C_1$-$C_6$ alkyl or phenyl; $R^3$ is $C_1$-$C_6$ alkoxy, $C_1$-$C_6$ alkyl or $C_1$-$C_6$ alkylthio; $R^4$ is $C_1$-$C_6$ alkoxy, $C_1$-$C_6$ alkylthio, $C_1$-$C_6$ alkylamino or $C_1$-$C_6$ dialkylamino; and X is oxygen or sulfur.

10 Claims, No Drawings

OXIME PHOSPHATE PESTICIDAL COMPOUNDS, COMPOSITIONS AND METHODS

BACKGROUND OF THE INVENTION

1. Field of the Invention

The present invention is directed to a novel class of compounds that have utility as pesticides, particularly in the control of nematodes, insects and acarids. Thus, the present invention is particularly directed to a class of compounds which are effective as nematicides, insecticides and acaricides.

Pests, such as nematodes, insects and acarids, pose serious problems to agriculture. A wide variety of field crops are menaced by nematodes, insects and acarids. Such valuable crops as tobacco, corn, soybeans, peanuts, citrus, potato and sugar beets all require protection from the ravages of nematodes, insects, and acarids.

Of particular concern is the protection of tobacco, soybeans and peanuts. These are important commercial crops. Those skilled in the art are aware that these crops are subject to destruction from soil pests, especially the root knot nematode. Nematodes invade and cause severe damage to the roots of such plants. Protection against nematodes is particularly acute in the absence of crop rotation. Plants attacked by this nematode produce lower yields and significant crop loss may result.

Nematicidal compounds with insecticidal activity against soil larvae such as wireworms, cutworms and rootworms, against sucking pests such as aphids, and against foliar feeding beetles and mites provide more complete plant protection. It is appreciated that there are known methods for non-fumigant control of nematodes, insects and mites. However, these methods, the most common of which is the application of carbamate and organophosphorus compounds, are being eliminated because of the high levels of mammalian toxicity in several products. It is highly important to emphasize the requirement that any soil pesticide which is employed be capable of being applied in sufficiently low concentration to ensure environmental safety.

2. Description of Related Art

U.S. Pat. Nos. 4,327,090; 4,424,215; 4,568,668; 4,612,306; and 4,670,425 are directed to various classes of oximinophosphoric acid derivatives said to have application as pesticides. All of these derivatives are formed by reacting a thiono or thiol phosphoric or phosphonic acid ester or amide halide with a compound which provides the derivative portion of the oximinophosphoric acid derivative compound. These compounds include an alpha-cyano group. None of the compounds includes a tetrazolidinone ring.

U.S. Pat. No. 4,330,536 is directed to oxime phosphates which include pyridyloxy benzaldehyde groups. Moreover, a tetrazolinone ring is not part of the oxime phosphate structure.

U.S. Pat. No. 4,339,444 is directed to oxime phosphate compounds said to have insecticidal, miticidal and nematicidal activity. The compounds have an alpha-alkoxy substituent. The inclusion of this substituent in an oxime phosphate compound is distinguished from an oxime phosphate compound which includes a tetrazolidinone ring.

U.S. Pat. No. 4,535,077 is directed to O-ethyl S,S-dialkyl phosphorodithioates said to be effective against soil borne insects and nematodes. Those compounds are completely structurally removed from an oxime phosphate compound.

U.S. Pat. No. 4,618,365 is directed to a substituted tetrazolinone said to be useful as a preemergence and postemergence herbicide. Those compounds, however, are remote from oxime phosphate compounds, and do not include phosphorus atoms.

U.S. Pat. No. 4,839,439 is directed to a class of phosphorus substituted tetrazolinone compounds said to be useful in pesticidal compositions.

The above remarks establish the need in the art for a new class of compounds, useful as a pesticide, especially against soil insects, nematodes and acarids that can control these harmful pests over long periods of time, albeit at very low concentrations.

SUMMARY OF THE INVENTION

A new class of compounds has been discovered which provides long-term control of pests, such as insects, nematodes and acarids, in a low concentration. This effectiveness is particularly noted against such soil inhabiting pests as soil insects, nematodes and acarids. Its use in controlling nematodes is of particular commercial importance.

In accordance with the present invention a compound having the structural formula $$\underset{N=N}{R-N\diagdown\overset{\displaystyle\overset{O}{\|}}{\diagup}N}-\underset{|}{\overset{R^1}{C}}H-\underset{|}{\overset{R^2}{C}}=NO\overset{X}{\overset{\|}{P}}\diagdown\overset{R^3}{\diagup}R^4 \qquad I$$

where R is lower alkyl, phenyl, substituted phenyl, naphthyl or substituted naphthyl; $R^1$ is hydrogen or $C_1$-$C_6$ alkyl; $R^2$ is $C_1$-$C_6$ alkyl or phenyl; $R^3$ is $C_1$-$C_6$ alkoxy, $C_1$-$C_6$ alkyl or $C_1$-$C_6$ alkylthio; $R^4$ is $C_1$-$C_6$ alkoxy, $C_1$-$C_6$ alkylthio, $C_1$-$C_6$ alkylamino or $C_1$-$C_6$ dialkylamino; and X is oxygen or sulfur.

In further accordance with the present invention, a composition is provided comprising a pesticidally effective amount of the compound of the present invention and a suitable carrier therefor.

In further accordance with the present invention a process for controlling pests is provided wherein a pesticidally effective amount of the compound of the present invention is applied to the loci to be controlled.

DETAILED DESCRIPTION OF THE INVENTION

The present invention is directed to a compound having the structural formula $$\underset{N=N}{R-N\diagdown\overset{\displaystyle\overset{O}{\|}}{\diagup}N}-\underset{|}{\overset{R^1}{C}}H-\underset{|}{\overset{R^2}{C}}=NO\overset{X}{\overset{\|}{P}}\diagdown\overset{R^3}{\diagup}R^4 \qquad I$$

where R is lower alkyl, phenyl, substituted phenyl, naphthyl or substituted naphthyl; $R^1$ is hydrogen or $C_1$-$C_6$ alkyl; $R^2$ is $C_1$-$C_6$ alkyl or phenyl; $R^3$ is $C_1$-$C_6$ alkoxy, $C_1$-$C_6$ alkyl or $C_1$-$C_6$ alkylthio; $R^4$ is $C_1$-$C_6$ alkoxy, $C_1$-$C_6$ alkylthio, $C_1$-$C_6$ alkylamino or $C_1$-$C_6$ dialkylamino; and X is oxygen or sulfur.

Preferably, the compound having the structural formula I is characterized by R being $C_1$-$C_4$ alkyl or phenyl; $R^1$ being hydrogen or methyl; $R^2$ being $C_1$-$C_2$ alkyl or phenyl; $R^3$ being $C_1-C_4$ alkylthio or $C_1-C_4$ alkoxy; $R^4$ being $C_1-C_4$ alkoxy, $C_1-C_4$ alkylamino or $C_1-C_4$ alkylthio; and X being oxygen or sulfur.

More preferably, the compound of the present invention has the structural formula I where R is methyl; $R^1$ is hydrogen; $R^2$ is methyl or phenyl; $R^3$ is ethoxy or butylthio; $R^4$ is $C_1-C_4$ alkylamino; ethoxy or butylthio; and X is oxygen or sulfur.

Of particular interest ar such compounds having the structural formula I, characterized by R being methyl, $R^1$ being hydrogen, $R^2$ being methyl, $R^3$ being ethoxy, $R^4$ ethoxy and X being sulfur. Another such compound is defined by structural formula I in which R is methyl, $R^1$ is hydrogen, $R^2$ is phenyl, $R^3$ is ethoxy, $R^4$ is ethoxy and X is sulfur. Yet another such compound having the structural formula I is distinguished by R being methyl; $R^1$ being hydrogen, $R^2$ being methyl, $R^3$ being ethoxy, $R^4$ being sec-butylthio and X being oxygen.

The compounds of the present invention are particularly useful in the formation of pesticidal compositions. The pesticidal composition of the present invention comprises the compound having the structural formula I, present in a pesticidally effective amount, and an agriculturally acceptable carrier therefor.

A carrier useful in the composition of this invention may be liquid, solid or mixtures thereof. Suitable liquid carriers include water, aliphatic organic compounds such as alcohols or ketones and aromatic organic compounds such as phenols, toluene and xylenes.

These liquid carriers may be added to form solutions in the case where liquid dissolves the active compound, the compound having the structural formula I. Alternatively, in the case where the carrier is insoluble in the compound having the structural formula, I, the liquid composition is a dispersion. Thus, water and other polar organic compounds in which the compound I does not dissolve are employed in this fashion.

Yet another liquid composition is an emulsion. Aqueous emulsions are obtained by combining the compound having the structural formula I with water in the presence of a surface active dispersing agent which may be non-ionic, cationic or anionic. Surface active agents within the contemplation of the present invention are disclosed in U.S. Pat. No. 2,547,724, incorporated herein by reference. The compounds of the present invention may be mixed with such surface active dispersing agents, with or without an organic solvent, as concentrates for the subsequent addition of water to yield aqueous suspensions of the active compounds at desirable concentration levels.

Another liquid carrier that may be utilized is an aerosol. In this application the compound having the structural formula I is dissolved in an aerosol carrier which is liquid under pressure but which is a gas at ordinary temperature and pressure. The aerosol formulation may, in a preferred embodiment, be first prepared by first dissolving the active compound in a less volatile solvent and then admixing the resultant solution with a highly volatile liquid aerosol carrier.

Additives conventionally employed in the art may be provided with these liquid carriers to facilitate particular applications of the resulting pesticidal composition. Thus, surface active agents, already mentioned earlier, diluents and mixtures thereof may be added to the liquid carrier to form the liquid composition.

Solid carriers useful in the formation of pesticidal compositions within the scope of this invention include dusts, granules, wettable powders, pastes and water soluble solids. For example, the pesticidal composition of this invention may be applied as a dust when admixed with, adsorbed or absorbed onto a powdered solid carrier such as a mineral silicate, e.g., mica, talc, pyrophyllite and clays. When a surface-active dispersing agent is added to such a composition, a wettable powder is obtained.

Additional solid compositions can be prepared from granular formulations of the active compound using a granular or pelletized form of carrier such as a granular clay, vermiculite, charcoal, corn cobs, or the like. Such granular formulations are particularly suitable for application by broadcasting, side dressing, soil incorporation or seed treatment.

A mixture of a solid and liquid composition may be prepared by dispersing solids, upon which the active compounds are absorbed or adsorbed, in a liquid dispersant. Such a composition may include a surface active agent to maintain the solid particles dispersed in the liquid dispersant.

Finally, the pesticidal composition of the present invention may utilize a carrier which is itself pesticidally active, such as an insecticide, an acaricide, a fungicide or a bacteriacide.

As stated above, the concentration of the compound having structural formula I in the composition of this invention is a pesticidally effective amount. A pesticidal effective amount depends upon the specific pest to be combated as well as the identity of the specific carrier utilized to apply the active compound. As such, the pesticidally effective amount of the compound varies widely. Generally, the concentration of the active ingredient representative of a pesticidally effective amount in the composition of the present invention may range from about 0.1% to about 95% by weight. Spray dilutions, however, may be as low as a few parts of active compound per million parts of composition. On the other hand, when ultra-low volume applications are utilized, full strength concentrates may be applied.

Although the active compound, provided as a composition, may be sprayed onto the pests and/or plant upon which the pests feed or nest directly, the compounds of the present invention are preferably applied to the soil in which the pests are present.

The present invention is also directed to a process for controlling harmful pests such as insects, nematodes and acarids, particularly those found in the soil. These pests attack a wide variety of plants by inflicting damage by consuming roots and/or foliage, withdrawing vital juices from the plants, secreting toxins and often by transmitting diseases. As stated earlier, the compounds of the present invention are advantageously utilized to minimize or prevent such damage. In the process, a pesticidally effective amount of the active compound is applied to the locus to be protected. In a particularly preferred embodiment of the process of the present invention, a pesticidally effective amount of compound I is applied to the soil in which the plants to be protected are grown and where the target pests are found. Of particular importance is the control of soil pests such as nematodes and the like which are controlled by the process of the present invention.

As stated above, the process of inhibiting soil insects, nematodes and acarids involve the introduction of a pesticidally effective amount of the compounds of the present invention to the soil in which the plants to be protected are grown. The definition of what constitutes a pesticidally effective amount necessary to control soil pests varies with the plant to be protected, the soil constituency, climatic conditions and the like. Generally, between about 0.01 and about 50 pounds of the active compound may be introduced per acre of soil. Usually, between about 0.1 and about 10 pounds of the compound is utilized per acre when commercially important crops such as corn, tobacco, rice and the like, are the plants to be protected.

The compound having the structural formula I may be prepared by reacting a halophosphate having the structural formula

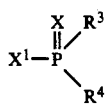

where X, $R^3$ and $R^4$ are as defined in compound I and $X^1$ is halogen, preferably chlorine, with an oxime having the structural formula

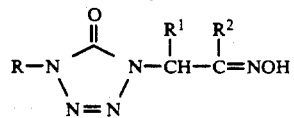

where R, $R^1$ and $R^2$ have the meanings given for compound I.

The reaction of compound II with compound III is preferably conducted in a polar solvent in the presence of an acid-acceptor. Thus, acetone, acetonitrile or the like, are used as the polar solvent. Preferred acid-acceptors include potassium carbonate and triethylamine.

Halophosphates, within the contemplation of compound II, especially chlorophosphates, are commercially available. Those not commercially available can be prepared by methods set forth in U.S. Pat. No. 4,535,077, which is incorporated herein by reference. That patent teaches the preparation of O-ethyl S-alkyl phosphorothioic chloride by reacting S-alkyl phosphorothioic dichloride with ethanol.

The oxime compound having the structural formula III is prepared by reacting the corresponding ketone with hydroxylamine hydrochloride in the presence of a hydrogen chloride acceptor such as pyridine. The ketone utilized in the formation of compound III is itself prepared by reacting an alpha-halo ketone with a tetrazolinone in the presence of an acid-acceptor. Acid acceptors useful in this reaction include potassium carbonate, pyridine and triethylamine. The tetrazolinones utilized in the formation of the ketone are known in the art. Preparation of tetrazolinones are taught in such publications as Tsuge et al., J. Org. Chem., 45, 5130 (1980); Horwitz et al., J. Amer. Chem. Soc., 81, 3076 (1959); and U.S. Pat. Nos. 4,618,365 and 4,839,349. All of these disclosures are incorporated herein by reference.

An alternate method of preparing compounds having the structural formula I constitutes the reaction of the oxime compound having the structural formula I with a phosphorothioic dichloride or a dichlorophosphate to yield an oxime chlorophosphate. That product is reacted with an alcohol, mercaptan or amine to provide the desired product.

Phosphonates of this invention (where $R^3$=alkyl) can be prepared by one of the above procedures (e.g. see U.S. Pat. No. 4,327,090, cited above) or alternatively by reacting an oxime, III, with a thionophosphine sulfide having the structure

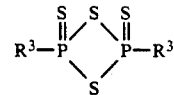

Thionophosphine sulfides are known in the literature and can be prepared as described in J. Org. Chem. 1962, 27, 3829.

The following examples are given to illustrate the scope of the present invention. Because these examples are given for illustrative purposes only, the invention should not be limited thereto.

EXAMPLE 1

Preparation of 4-(2-Oxopropyl)-1-methyl-5(4H)tetrazolinone

1-Methyl-5(4H)tetrazolinone (50 g., 0.5 mol) was dissolved in 500 ml of acetone and 69 g. (0.5 mol) of anhydrous potassium carbonate was added with stirring. The mixture was refluxed for 0.5 hour. There was a gas evolution and a thick white precipitate formed. The mixture was cooled to 10° C. and 49.7 ml (57.8 g, 0.625 mol) of chloroacetone was added in one portion. The reaction mixture was refluxed for 6 hours, cooled, and allowed to stand overnight. After filtration, the dark red solution was evaporated to dryness, giving 86.5 g. of crude product. Recrystallization from isopropyl alcohol gave 58.8 g. of tan crystals, mp 90°–91.5° C. A second crop was obtained giving a total yield of 62.9 g. (81%). The structure was confirmed by infrared and nuclear magnetic resonance spectroscopy.

EXAMPLE 2

Preparation of 4-(2-Oxopropyl)-1-methyl-5(4H)-tetrazolinone oxime 4-(2-Oxopropyl)-1-methyl-5(4H)tetrazolinone (31.2 g., 0.2 mol) and 75 ml of pyridine were combined and 17.4 g (0.25 mol) of hydroxylamine hydrochloride was added in one portion. The reaction was somewhat exothermic. The reaction mixture was heated at reflux for two hours and then stripped using a vacuum pump to remove the excess pyridine. Addition of water (about 30 ml) caused precipitation of the product which was isolated by filtration. Total yield was 29.9 g. (87%). IR and NMR were used to confirm the structure of the product.

EXAMPLE 3

S-(2-Butyl) O-[2-(4,5-Dihydro-4-methyl-5-oxo-1H-tetrazole-1-yl)-1-methylethylidinimino]chlorothiophosphate 4-(2-Oxopropyl)-1-methyl-5(4H)tetrazolinone oxime (2.73 g. 0.016 mol), 20 ml of toluene and 1.29 ml (1.26 g. 0.16 mol) of pyridine were combined at room temperature and 3.31 g. (0.016 mol) of S-2-butyl phosphorothioic dichloride was added dropwise during 5 minutes. There was a slight exotherm. The mixture was stirred for three hours at room temperature and then washed three times with 30 ml portions of water. The organic layer was dried over magnesium sulfate and stripped to remove solvents to 42° C. (0.22mm) giving a thick amber oil, wt. 4.57 g (84%). The structure was confirmed using IR and NMR spectra.

EXAMPLE 4

Preparation of O-Ethyl S-(sec-butyl) O-[2-(4,5-dihydro-4-methyl-5-oxo-1H-tetrazol-1-yl)-1-methylethylidiniminol-phosphorothioate (Compound No. 3)

S-(2-Butyl) O-[2-(4,5-dihydro-4-methyl-5-oxo-1H-tetrazol-1-yl)-1-methylethylidinimino] chlorothiosphosphate (4.54 g, 0.0133 mol) was dissolved in 20 ml of toluene and 1.76 ml (1.38 g, 0.03 mol) of ethanol was added in one portion, followed by 1.13 ml (1.11 g, 0.014 mol) of pyridine at room temperature. There was a slight exotherm and the mixture was warmed to 45°–47° C. for 2.5 hours, then allowed to stand overnight at room temperature. The mixture was washed three times with 10 ml portions of water. The toluene solution was dried and stripped to 47° C. (0.25 mm) giving the product as a light amber oil, wt. 3.77 grams (81%). IR and NMR indicated that it had the desired structure.

EXAMPLE 5

Preparation of O-Ethyl S-sec-butyl phosphorothioic chloride

A solution of 41.4 g (0.20 mol) of S-2-Butyl phosphorothioic dichloride in 200 ml of toluene was cooled to 0° C. and 17.6 ml (13.8 g, 0.30 mol) of absolute ethanol was added in one portion. Pyridine (16.2 ml, 15.8 g, 0.20 mol) was added dropwise during 5 minutes maintaining a maximum temperature of 13° C. When the addition was complete, the mixture was allowed to warm to room temperature and was stirred for 1.5 hours. The insoluble salt was removed by filtration and the solvent was stripped from the filtrate. Additional salt was removed after addition of ether. The product was distilled as a colorless oil, bp 73°–75° C. (9.17 mm). Some white solid co-distilled and was separated by decantation. The yield was 37.4 g (86%).

EXAMPLE 6

Preparation of O-Ethul S-(2-butyl) O-[2-(4,5-dihydro-4-methyl-5-oxo-1H-tetrazol-1-yl)-1-methylethylidinimol phosphorothioate (Compound No. 3)

4-(2-Oxopropyl)-1-methyl-5-(4H)tetrazolinone oxime (5.13 g, 0.03 mol) and 7.79 g (0.036 mol) O-ethyl S-2-butyl phosphorothioic chloride were combined in 90 ml of acetone. Anhydrous potassium carbonate (4.97 g, 0.036 mol) was ground to a fine powder and added gradually over a period of 1.75 hours. The mixture was heated to reflux for 2 hours, cooled, and allowed to stand overnight at room temperature. The reaction mixture was filtered to remove salts and the solvent was removed from the filtrate. The resulting crude oil was taken up in ether and the solution was washed with three 20 ml portions of water. The solution was dried, filtered and concentrated at 45° C. (0.2 mm) to give 8.59 g of crude product, which was purified by flash chromatography to yield 2.40 g (23%) of product as a pale yellow viscous oil. IR and NMR confirmed the structure.

EXAMPLE 7

Preparation of N-(1-Propyl) S-(2-butyl) O-2-(4,5-dihydro-4-methyl-5-oxo-1H-tetrazol-1-yl)-1-methylethylidinimino]-phosphoramidothioate (Compound No. 14)

4-(2-Oxopropyl)-1-methyl-5(4H-tetrazolinone) oxime (1.71 g, 0.01 mol), 10 ml of toluene and (0.79 g, 0.01 mol) of pyridine were combined at room temperature and (2 07 g, 0.01 mol) of S-2-butyl phosphorothioic dichloride was added in one portion. There was a slight exotherm. The mixture was warmed to 50° C. and held for one hour, then cooled to room temperature and a solution of 1.90 g (0.032 mol) n-propyl amine dissolved in 5 ml of toluene was added in one portion. There was a slight exotherm. The mixture was warmed to 50° C. and held for one hour, then cooled to room temperature and stirred for an additional hour. The mixture was washed with 15 ml of water. The toluene solution was dried and stripped to give crude product as a dark amber oil, weighing 3.00 g (82%). This crude product was then dissolved in toluene and put through a small silica gel column to give pure product as a light amber oil, weighing 2.58 g (71%). NMR confirmed that it had the desired structure.

EXAMPLE 8

Preparation of Compound Nos. 1, 2, 4–13 and 15–40

Additional compounds within the scope of generic structural formula I were prepared, using the methods described in Examples 1 to 7. Structures were confirmed by nuclear magnetic resonance and infrared spectroscopy. These compounds are summarized, as are Compounds Nos. 3 and 14, discussed in the earlier examples, in Tables I and II. Table I identifies the compounds made in accordance with these examples. Table II provides nuclear magnetic resonance (NMR) spectroscopy data for each of the compounds shown in Table I.

EXAMPLE 9

Preparation of S-Methyl-O-[2-(4,5-dihydro-4-ethyl-5-oxo-1H-tetrazol-1-yl)-1-methylethylidinimino]methylphosponodithioate Methyl thionophosphine sulfide (1.10g, 0.005 mol) and tetrahydrofuran (12.5ml) were combined at room temperature. The mixture was then cooled to 0° C. and 4-(2-Oxopropyl)-1-ethyl-5(4H)-tetrazolinone oxime (1.85 g, 0.01 mol) was added. After a few minutes the mixture turned very dark and after one hour at 0°–5° C. triethylamine (1.06 g, 0.0105 mol) was added. An exotherm to 10° was observed. The mixture was then cooled back down to 5° C. and stirred for 2 hours. During that period, the color of the mixture changed from a dark orange to a light orange. Iodomethane (1.56g, 0.011 mol) was added. The whole was permitted to warm to room temperature and stirred overnight. Solvent was then stripped off. Chloroform and water were added to the residue. After mixing, the chloroform layer was separated out. The chloroform solution was then poured through a short silica gel column and stripped of solvent. This crude product was purified by flash chromatography to yield 1.03g (33%) of pure product; a clear amber oil. IR and NMR confirmed structure.

TABLE I

| Cmpd. No. | R | R1 | R2 | R3 | R4 | X |
|---|---|---|---|---|---|---|
| 1 | $CH_3$ | H | $CH_3$ | $OC_2H_5$ | $OC_2H_5$ | O |
| 2 | $CH_3$ | H | $CH_3$ | $OC_2H_5$ | $S\text{-}i\text{-}C_3H_7$ | O |
| 3 | $CH_3$ | H | $CH_3$ | $OC_2H_5$ | $S\text{-}i\text{-}C_4H_9$ | O |
| 4 | $CH_3$ | H | $CH_3$ | $SC_2H_5$ | $S\text{-}i\text{-}C_3H_7$ | O |
| 5 | $CH_3$ | H | $CH_3$ | $SC_2H_5$ | $O\text{-}i\text{-}C_3H_7$ | O |
| 6 | $CH_3$ | H | $CH_3$ | $S\text{-}i\text{-}C_3H_7$ | $S\text{-}i\text{-}C_3H_7$ | O |
| 7 | $CH_3$ | H | $CH_3$ | $S\text{-}i\text{-}C_3H_7$ | $O\text{-}n\text{-}C_3H_7$ | O |
| 8 | $CH_3$ | H | $CH_3$ | $S\text{-}I\text{-}C_3H_7$ | $O\text{-}i\text{-}C_3H_7$ | O |
| 9 | $CH_3$ | H | $CH_3$ | $S\text{-}i\text{-}C_3H_7$ | $NH\text{-}n\text{-}C_4H_9$ | O |
| 10 | $CH_3$ | H | $CH_3$ | $S\text{-}s\text{-}C_4H_9$ | $OCH_3$ | O |
| 11 | $CH_3$ | H | $CH_3$ | $S\text{-}s\text{-}C_4H_9$ | $O\text{-}n\text{-}C_3H_7$ | O |
| 12 | $CH_3$ | H | $CH_3$ | $S\text{-}s\text{-}C_4H_9$ | $O\text{-}i\text{-}C_3H_7$ | O |
| 13 | $CH_3$ | H | $CH_3$ | $S\text{-}s\text{-}C_4H_9$ | $O\text{-}n\text{-}C_4H_9$ | O |
| 14 | $CH_3$ | H | $CH_3$ | $S\text{-}s\text{-}C_4H_9$ | $NH\text{-}n\text{-}C_3H_7$ | O |
| 15 | $CH_3$ | H | $CH_3$ | $OC_2H_5$ | $OC_2H_5$ | S |
| 16 | $C_2H_5$ | H | $CH_3$ | $OC_2H_5$ | $S\text{-}s\text{-}C_4H_9$ | O |
| 17 | $C_6H_5$ | H | $CH_3$ | $OC_2H_5$ | $S\text{-}s\text{-}C_4H_9$ | O |
| 18 | $C_6H_5$ | H | $CH_3$ | $OC_2H_5$ | $S\text{-}s\text{-}C_3H_7$ | O |
| 19 | $CH_3$ | $CH_3$ | $CH_3$ | $OC_2H_5$ | $S\text{-}i\text{-}C_3H_7$ | O |
| 20 | $CH_3$ | H | $C_6H_5$ | $OC_2H_5$ | $OC_2H_5$ | S |
| 21 | $CH_3$ | H | $C_6H_5$ | $OC_2H_5$ | $S\text{-}s\text{-}C_4H_9$ | O |
| 22 | $C_6H_5$ | H | $CH_3$ | $S\text{-}s\text{-}C_4H_9$ | $NH\text{-}n\text{-}C_3H_7$ | O |
| 23 | $C_6H_5$ | H | $CH_3$ | $S\text{-}s\text{-}C_4H_9$ | $NH\text{-}i\text{-}C_3H_7$ | O |
| 24 | $C_2H_5$ | H | $CH_3$ | $S\text{-}s\text{-}C_4H_9$ | $NH\text{-}n\text{-}C_3H_7$ | O |
| 25 | $CH_3$ | H | $CH_3$ | $S\text{-}s\text{-}C_4H_9$ | $NH\text{-}C_2H_5$ | O |
| 26 | $CH_3$ | H | $CH_3$ | $S\text{-}i\text{-}C_2H_7$ | $NH\text{-}C_2H_5$ | O |
| 27 | $CH_3$ | H | $CH_5$ | $S\text{-}s\text{-}C_4H_9$ | $N(CH_3)_2$ | O |
| 28 | $CH_3$ | H | $CH_3$ | $S\text{-}s\text{-}C_4H_9$ | $NH_2$ | O |
| 29 | $2\text{-}C_2H_5O\text{-}C_6H_4$ | H | $CH_3$ | $S\text{-}s\text{-}C_4H_9$ | $OC_2H_5$ | O |
| 30 | $2\text{-}C_2H_5\text{-}C_6H_4$ | H | $CH_3$ | $S\text{-}s\text{-}C_4H_9$ | $OC_2H_5$ | O |
| 31 | $3,4\text{-di-}CH_3\text{-}C_6H_3$ | H | $CH_3$ | $S\text{-}s\text{-}C_4H_9$ | $OC_2H_5$ | O |
| 32 | $4\text{-}F\text{-}C_6H_4$ | H | $CH_3$ | $S\text{-}s\text{-}C_4H_9$ | $OC_2H_5$ | O |
| 33 | $2\text{-}C_2H_5O\text{-}C_6H_4$ | H | $CH_3$ | $S\text{-}s\text{-}C_4H_9$ | $NH\text{-}n\text{-}C_3H_7$ | O |
| 34 | $2\text{-}C_2H_5\text{-}C_6H_4$ | H | $CH_3$ | $S\text{-}s\text{-}C_4H_9$ | $NH\text{-}n\text{-}C_3H_7$ | O |
| 35 | $3,4\text{-di-}CH_3\text{-}C_6H_3$ | H | $CH_3$ | $S\text{-}s\text{-}C_4H_9$ | $NH\text{-}i\text{-}C_3H_7$ | O |
| 36 | $4\text{-}F\text{-}C_6H_4$ | H | $CH_3$ | $S\text{-}s\text{-}C_4H_9$ | $NH\text{-}i\text{-}C_3H_7$ | O |
| 37 | $2\text{-}C_2H_5O\text{-}C_6H_4$ | H | $CH_3$ | $S\text{-}i\text{-}C_3H_7$ | $NH\text{-}i\text{-}C_3H_7$ | O |
| 38 | $C_2H_5$ | H | $CH_3$ | $S\text{-}s\text{-}C_4H_9$ | $NH_2$ | O |
| 39 | $C_6H_5$ | H | $CH_3$ | $S\text{-}s\text{-}C_4H_9$ | $NH_2$ | O |
| 40 | $C_2H_5$ | H | $CH_3$ | $CH_3$ | $SCH_3$ | S |

TABLE II

| Cmpd. No. | NMR Data<br>NMR $CDCl_3$ (300 MHz) |
|---|---|
| 1 | 1.35(t, 6H), 2.02(s, 3H), 3.65(s, 3H), 4.15–4.30(m, 4H), 4.75(s, 2H) |
| 2 | 1.29–1.47(m, 9H), 2.01(s, 3H), 3.63(s, 3H), 3.40–3.55(m, 1H), 4.10–4.30(m, 2H), 4.76(s, 2H) |
| 3 | 0.98–1.05(m, 3H), 1.32–1.48(m, 6H), 1.66–1.79(m, 2H), 2.01(s, 3H), 3.39–3.52(m, 1H), 3.64(s, 3H), 4.19–4.31(m, 2H), 4.75(s, 2H) |
| 4 | 1.24–1.37(m, 9H), 1.90(s, 3H), 2.80–2.95(m, 2H), 3.52(s, 3H), 3.45–3.60(m, 1H), 4.65(s, 2H) |
| 5 | 1.34–1.45(m, 9H), 2.01(s, 3H), 2.88–3.03(m, 2H), 3.65(s, 3H), 4.76(s, 2H), 4.81–4.93(m, 1H) |
| 6 | 1.40–1.50(m, 6H), 2.02(s, 3H), 3.65(s, 3H), 3.55–3.70(m, 1H), 3.85(d, 3H), 4.75(s, 2H) |
| 7 | 0.93–1.03(m, 3H), 1.40–1.50(m, 6H), 1.68–1.80(m, 2H), 2.01(s, 3H), 3.65(s, 3H), 3.55–3.70(m, 1H), 4.14 (q, 2H), 4.75(s, 2H) |
| 8 | 1.35–1.55(m, 12H), 2.02(s, 3H), 3.65(s, 3H), 3.55–3.70(m, 1H), 4.76(s, 2H), 4.80–4.94(m, 1H) |
| 9 | 0.88–0.97(m, 3H), 1.25–1.55(m, 10H), 2.00(s, 3H), 2.95–3.10(m, 2H), 3.12–3.25(m, 1H), 3.50–3.62(m, 1H), 3.65(s, 3H), 4.74(s, 2H) |
| 10 | 0.98–1.08(m, 3H), 1.41–1.50(m, 3H), 1.66–1.80(m, 2H), 2.03(s, 3H), 3.39–3.52(m, 1H), 3.65(s, 3H), 3.85(d, 3H), 4.76(s, 2H) |
| 11 | 0.94–1.07(m, 6H), 1.40–1.49(m, 3H), 1.65–1.80(m, 4H), 2.02(s, 3H), 3.37–3.54(m, 1H), 3.65(s, 3H), 4.12(q, 2H), 4.75(s, 2H) |
| 12 | 0.97–1.07(m, 3H), 1.35–1.50(m, 9H), 1.65–1.80(m, 2H), 2.02(s, 3H), 3.39–3.54(m, 1H), 3.65(s, 3H), 4.76(s, 2H), 4.80–4.95(m, 1H) |
| 13 | 0.90–1.08(m, 6H), 1.38–1.50(m, 5H), 1.65–1.80(m, 4H), 2.02(s, 3H), 3.39–3.53(m, 1H), 3.65(s, 3H), 4.18(q, 2H), 4.75(s, 2H) |
| 14 | 0.80–1.05(m, 6H), 1.44(d, 3H), 1.50–1.60(m, 2H), 1.65–1.76(m, 2H), 2.00(s, 3H), 2.95–3.08(m, 2H), 3.12–3.25(m, 1H), 3.33–3.47(m, 1H), 3.65(s, 3H), 4.75(s, 2H) |
| 15 | 1.34(t, 6H), 2.02(s, 3H), 3.65(s, 3H), 4.15–4.28(m, 4H), 4.76(s, 2H) |
| 16 | 0.98–1.07(m, 3H), 1.33–1.52(m, 9H), 1.65–1.80(m, 2H), 2.02(s, 3H), 3.39–3.53(m, 1H), 3.96–4.09(m, 2H) 4.19–4.33(m, 2H), 4.75(s, 2H) |
| 17 | 0.95–1.05(m, 3H), 1.32–1.50(m, 6H), 1.61–1.80(m, 2H), 2.07(s, 3H), 3.39–3.54(m, 1H), 4.17–4.37(m, 2H), 4.85(s, 2H), 7.35–7.57(m, 3H), 7.88–7.99(m, 2H) |
| 18 | 1.31–1.45(m, 9H), 2.07(s, 3H), 3.53–3.68(m, 1H), 4.18–4.28(m, 2H), 4.85(s, 2H), 7.35–7.41(m, 1H), 7.47–7.55(m, 2H), 7.91–7.96(m, 2H) |
| 19 | 1.34–1.47(m, 9H), 1.75(d, 3H), 1.99(s, 3H), 3.64(s, 3H), 3.55–3.70(m, 1H), 4.19–4.30(m, 2H), 5.05–5.15(m, 1H) |
| 20 | 1.37(t, 6H), 3.52(s, 3H), 4.22–4.37(m, 4H), 5.29(s, 2H), 7.35–7.45(m, 3H), 7.65–7.69(m, 2H) |
| 21 | 0.98–1.08(m, 3H), 1.38–1.50(m, 6H), 1.68–1.82(m, 2H), 3.55(s, 3H), 3.47–3.60(m, 1H), 4.27–4.40(m, 2H), 5.33(s, 2H), 7.35–7.48(m, 3H), 7.65–7.70(m, 2H) |
| 22 | 0.85–1.05(m, 6H), 1.35–1.45(m, 3H), 1.45–1.55(m, 2H), 1.62–1.76(m, 2H), 2.07(s, 3H), 2.90–3.05(m, 2H), 3.10–3.24(m, 1H), 3.30–3.47(m, 1H), 4.85(s, 2H), 7.35–7.58(m, 3H), 7.90–8.00(m, 2H) |
| 23 | 0.93–1.02(m, 3H), 1.14–1.20(d, 6H), 1.37–1.43(d, 3H),1.60–1.78(m, 2H), 2.06(s, 3H), 2.90–3.03(m, 1H), 3.30–3.47(m, 1H), 3.47–3.64(m, 1H), 4.83(s, 2H), 7.35–7.43(m, 1H), 7.47–7.53(m, 2H), 7.90–7.98(m, 2H) |
| 24 | 0.85–1.05(m, 6H), 1.30–2.05(m, 13H), 2.87–3.07(m, 2H), 3.26–3.55(m, 2H), 3.98–4.08(m, 2H), 4.75(s, 2H) |
| 25 | 0.93–1.05(m, 3H), 1.12–1.22(m, 3H), 1.40–1.47(d, 3H), 1.61–1.80(m, 2H), 2.02(s, 3H), 2.95–3.15(m, 2H), 3.32–3.45(m, 1H), 3.45–3.55(m, 1H), 3.65(s, 3H), 4.75(s, 2H) |
| 26 | 1.14–1.22(m, 3H), 1.41–1.48(d, 6H), 2.02(s, 3H), 3.00–3.17(m, 2H), 3.36–3.50(m, 1H), 3.50–3.62(m, 1H), 3.65(s, 3H), 4.75(s, 2H) |
| 27 | 0.97–1.07(m, 3H), 1.39–1.49(m, 3H), 1.64–1.80(m, 2H), 2.00(s, 3H), 2.72–2.78(d, 6H), 3.34–3.48(m, 1H), |

TABLE II-continued

| Cmpd. No. | NMR Data NMR CDCl₃ (300 MHz) |
|---|---|
| | 3.65(s, 3H), 4.76(s, 2H) |
| 28 | 0.94–1.02(m, 3H), 1.38–1.46(m, 3H), 1.60–1.75(m, 2H), 2.02(s, 3H), 3.30–3.48(m, 1H), 3.64(s, 3H), 3.95–4.08(m, 2H), 4.78(s, 2H) |
| 29 | 0.96–1.08(m, 3H), 1.28–1.50(m, 9H), 1.65–1.78(m, 2H), 2.05(s, 3H), 3.40–3.55(m, 1H), 4.04–4.13(q, 2H), 4.22–4.34(m, 2H), 4.85(s, 2H), 7.02–7.10(m, 2H), 7.35–7.40(m, 1H), 7.42–7.50(m, 1H) |
| 30 | 0.97–1.05(m, 3H), 1.15–1.22(t, 3H), 1.34–1.50(m, 6H), 1.65–1.78(m, 2H), 2.08(s, 3H), 2.55–2.65(q, 2H), 3.40–3.55(m, 1H), 4.20–4.32(m, 2H), 4.86(s, 2H), 7.31–7.38(m, 2H), 7.38–7.51(m, 2H) |
| 31 | 0.95–1.05(m, 3H), 1.33–1.48(m, 6H), 1.65–1.77(m, 2H), 2.07(s, 3H), 2.28–2.36(d, 6H), 3.38–3.52(m, 1H), 4.19–4.31(m, 2H), 4.85(s, 2H), 7.21–7.27(d, 1H), 7.58–7.64(dd, 1H), 7.66–7.68(s, 1H) |
| 32 | 0.95–1.05(m, 3H), 1.33–1.47(m, 6H), 1.63–1.77(m, 2H), 2.08(s, 3H), 3.38–3.52(m, 1H), 4.19–4.30(m, 2H), 4.85(s, 2H), 7.15–7.25(m, 2H), 7.90–7.97(m, 2H) |
| 33 | 0.87–0.95(t, 3H), 0.95–1.05(m, 3H), 1.29–1.37(t, 3H), 1.41–1.46(d, 3H), 1.50–1.59(m, 2H), 1.65–1.80(m, 2H), 2.05(s, 3H), 2.95–3.08(m, 2H), 3.17–3.30(m, 1H), 3.35–3.48(m, 1H), 4.05–4.14(q, 2H), 4.82(s, 2H), 7.02–7.10(m, 2H), 7.35–7.40(m, 1H), 7.44–7.50(m, 1H) |
| 34 | 0.88–0.95(m, 3H), 0.95–1.05(m, 3H), 1.15–1.22(t, 3H), 1.41–1.47(d, 3H), 1.48–1.58(m, 2H), 1.65–1.80(m, 2H), 2.07(s, 3H), 2.55–2.65(q, 2H), 2.95–3.08(m, 2H), 3.12–3.24(m, 1H), 3.35–3.47(m, 1H), 4.85(s, 2H), 7.30–7.38(m, 2H), 7.38–7.51(m, 2H) |
| 35 | 0.93–1.03(m, 3H), 1.14–1.21(d, 6H), 1.38–1.45(d, 3H), 1.60–1.78(m, 2H), 2.05(s, 3H), 2.27–2.36(d, 6H), 2.90–3.08(m, 1H), 3.32–3.46(m, 1H), 3.50–3.68(m, 1H), 4.83(s, 2H), 7.22–7.27(d, 1H), 7.59–7.64(dd, 1H), 7.65–7.68(s, 1H) |
| 36 | 0.95–1.04(m, 3H), 1.15–1.21(d, 6H), 1.40–1.45(d, 3H), 1.62–1.78(m, 2H), 2.07(s, 3H), 2.90–3.05(m, 1H), 3.31–3.47(m, 1H), 3.50–3.65(m, 1H), 4.85(s, 2H), 7.18–7.25(m, 2H), 7.88–7.97(m, 2H) |
| 37 | 1.15–1.50(m, 15H), 2.05(s, 3H), 2.98–3.15(m, 1H), 3.50–3.70(m, 2H), 4.05–4.15(q, 2H), 4.83(s, 2H), 7.00–7.10(m, 2H), 7.35–7.42(m, 1H), 7.44–7.50(m, 1H) |
| 38 | 0.94–1.05(m, 3H), 1.37–1.50(m, 6H), 1.63–1.78(m, 2H), 2.04(s, 3H), 3.30–3.48(m, 1H), 3.65–3.80(m, 2H), 3.96–4.08(q, 2H), 4.75(s, 2H) |
| 39 | 0.93–1.05(m, 3H), 1.40–1.45(m, 3H), 1.63–1.78(m, 2H), 2.10(s, 3H), 3.33–3.52(m, 1H), 3.65–3.85(m, 2H), 4.86(s, 2H), 7.35–7.45(m, 1H), 7.45–7.57(m, 2H), 7.90–7.98(m, 2H) |
| 40 | 1.44–1.50(t, 3H), 2.02(s, 3H), 2.12–2.18(d, 3H), 2.38–2.46(d, 3H), 3.98–4.08(q, 2H), 4.75(s, 2H) |

Other compounds which can be made by these methods and are within the scope of the invention include:

O-Ethyl S-(2-butyl) O-[2-(4,5-dihydro-4-propyl-5-oxo-1H-tetrazol-1-yl)-1-methylethylidinimino]phosphorothiate;

O-Ethyl S-(2-butyl) O-[2-(4,5-dihydro-4-allyl-5-oxo-1H-tetrazol-1-yl)-1-methyl butylidinimino]phosphorothioate;

O-Ethyl S-methyl O-[2-(4,5-dihydro-4-methyl-5-oxo-1H-tetrazol-1-yl)-1-methylidinimino]phosphorothioate;

O-Methyl S-(2,2-dimethylpropyl) O-[2-(4,5-dihydro-4-methyl-5-oxo-1H-tetrazolmethylethylidinimino]-phosphorodithioate;

S-Methyl S-(2-propyl) O-(2-[4,5-dihydro-4-chlorophenyl)-5-oxo-1H-tetrazol-1-yl]-1-methylethylidinimino]phosphorothioate;

N-(2-Propyl) S-ethyl O-[2-[4,5-dihydro-4-(2-methylphenyl)-5-oxo-1H-tetrazol-1-yl]-1-methylethylininimino]phosphoramidothioate;

N-Methyl O-(2-propyl) O-[2-(4,5-dihydro-4-methyl-5-oxo-1H-tetrazol-1-yl)-1-methylethylidinimino]phosphoramidoate;

O-Ethyl S-(2-propyl) O-[2-[4,5-dihydro-4-(2,5-dimethoxyphenyl)-5-oxo-1H-tetrazol-1-yl]-1-methylethylidinimino]phosphorothioate;

O-(2-Propyl) S-methyl O-[2-(4,5-dihydro-4-cyclohexyl-5-oxo-1H-tetrazol-1-yl)-1-phenylethylidinimino]-phosphorothioate; and O-Methyl S-(2-butyl) O-[2-(4,5-dihydro-4-ethyl-5-oxo-1H-tetrazol-1-yl)-1-methyl-2-phenylethylidinimino]-phosphoramidothioate.

EXAMPLE 10

Control of Southern Corn Rootworm in Soil

Compound Nos. 3, 15 and 20, defined in Table I, were each tested to determine their effectiveness in the control of Southern corn rootworm. In this test, each of the tested compounds was formed into a water suspension composition. Each of the compounds was present in the composition in a concentration of 100 ppm. Each thus formed composition was added to four plastic pots, each pot holding 300 g. of soil. Specifically, 30 ml. of each of the water suspension compositions was added to each of the plastic pots. This treatment resulted in each pot containing a soil concentration of 10 ppm of one of Compound Nos. 3, 15 and 20.

All experiments were conducted with four replicates each, including controls which were not treated with the active compounds. Two corn seeds were planted in each pot. One week after planting, each pot was loaded with 10 corn rootworm larvae. One week after loading the pots with the larvae, scoring was undertaken by emptying the pots of their soil, filtering the soil through a fine mesh screen and recovering the larvae. The number of live larvae was counted, and percent control of Southern corn rootworm was calculated using Abbott's formula (J. Econ. Entomology, 18, 265–267 (1925)). It was found that each of these compounds provided 100% effectiveness.

EXAMPLES 11–15

Stock Solution Preparation

Stock solutions for the compounds were prepared at 3000 ppm (parts per million) by dissolving 0.3 gram of the compound to be tested in 10 ml of acetone and adding 90 ml of distilled water plus 4 drops of ethoxylated sorbitan monolaurate, a wetting agent.

Mite Test

The stock solution of 3000 ppm was diluted to 1000ppm. For each compound tested, primary leaves, one from each of two cowpeas (in one pot), were sprayed with an atomizer to thoroughly wet the foliage.

One day following treatment, groups of approximately 25 adult mites (*Tetranychus urticae* Koch) were transferred onto the upper surface of each leaf in areas created by the application of a circle of tree tanglefoot.

Five days following infestation with mites, the plants were examined for live mites remaining on the leaves. The percent control was estimated based on the number of mites surviving on the check plants.

The results of the testing of mites (MI) are given in Table II.

Nematode Test

The stock solution of 3000 ppm was diluted to 1000 ppm. For each compound, 25 ml was drenched onto 500 grams of soil infested with root knot nematode (*Meloidogyne incognita*) eggs in a pot, for a soil concentration of 50 ppm.

One day after treatment, two tomato seedlings were planted in each pot. Nineteen days after planting, the roots were evaluated for the presence of knots or galls, and the percent control was estimated based on the infestation levels in check plants.

The results of the testing of nematodes (NE) are given in Table II.

Rice Planthopper Foliar Test

The stock solution of 3000 ppm was diluted to 1000 ppm. One pot containing approximately 20 Mars variety rice seedlings was treated with each formulation by spraying with a spray atomizer. One day after treatment plants were covered with a tubular cage and twenty adult rice delphacids, *Sogatodes oryzicola*, were transferred into each cage. Five days after transferring, counts were made of the surviving planthoppers in each pot and percent control was estimated.

The results of the testing of the rice planthoppers (RPH) are given in Table II.

Southern Corn Rootworm Test

The stock solution of 3000 ppm was diluted to 100 ppm. For each compound, 2.5 ml was pipetted onto a Whatmann #3 filter paper at the bottom of a 100 mm petri dish. Two corn seedlings were soaked in the 100 ppm solution for 1 hour and transferred to the petri dish. After 24 hours, each dish was loaded with 5 second instar larvae of *Diabrotica undecimpunctata*. After 5 days, the number of live larvae were determined and the percent control, corrected by Abbott's formula, was calculated.

The results of the testing of southern corn rootworms (SCR) are given in Table II.

Tobacco Budworm Test

The stock solution of 3000 ppm was used for this test. For each compound, 0.2 ml was pipetted onto the surface of each of 5 diet cells, allowed to spread over the surfaces and air dried for 2 hours. Then a second instar *Heliothis virescens* larva was loaded into each cell. After 7 and 14 days, the number of live larvae was determined for each treatment and percent control, corrected by Abbott's formula, was calculated.

The results of the testing of tobacco budworms (TB) are given in Table III.

TABLE III

| CMPD. NO. | Percent Control | | | | |
|---|---|---|---|---|---|
| | MI | NE | RPH | SCR | TB |
| 1 | 0 | * | 0 | 11 | 0 |
| 2 | 100 | 100 | 75 | 100 | 20 |
| 3 | 100 | 100 | 100 | 100 | 40 |
| 4 | 0 | 70 | 25 | 0 | 0 |
| 5 | 0 | * | 0 | 0 | 0 |
| 6 | 100 | 90 | 55 | 100 | 58 |
| 7 | 30 | 50 | 30 | 79 | 0 |
| 8 | 0 | 60 | 0 | 0 | 0 |
| 9 | 70 | 0 | 0 | 0 | 0 |
| 10 | 100 | 100 | 90 | 100 | 100 |
| 11 | 0 | 100 | 75 | 100 | 0 |
| 12 | 50 | 50 | 40 | 58 | 0 |
| 13 | 50 | 100 | 40 | 100 | 16 |
| 14 | 90 | 100 | 95 | 100 | 0 |
| 15 | 70 | * | 75 | 100 | 0 |
| 16 | 100 | 0 | 85 | 100 | 80 |
| 17 | 100 | 100 | 95 | 100 | 80 |
| 18 | 95 | 95 | 50 | 100 | 100 |
| 19 | 100 | ** | 35 | 56 | 0 |
| 20 | 50 | 0 | 85 | 100 | 0 |
| 21 | 100 | 100 | 70 | 100 | 60 |
| 22 | 0 | 98 | 30 | 60 | 0 |
| 23 | 70 | 100 | 0 | 100 | 0 |
| 24 | 70 | 0 | 0 | 100 | 0 |
| 25 | 100 | *** | 100 | 100 | 0 |
| 26 | 100 | 70 | 85 | 20 | 0 |
| 27 | 95 | *** | 80 | 100 | 0 |
| 28 | 100 | 70 | 100 | 0 | 0 |
| 29 | 98 | 100 | 10 | 100 | 57 |
| 30 | 75 | 100 | 0 | 100 | 100 |
| 31 | 0 | 0 | 0 | 100 | 100 |
| 32 | 100 | 70 | 75 | 100 | 100 |
| 33 | 0 | 100 | 0 | 58 | 0 |
| 34 | 0 | 0 | 0 | 16 | 0 |
| 35 | 0 | 100 | 0 | 100 | 11 |
| 36 | 40 | 70 | 0 | 37 | 11 |
| 37 | 0 | 100 | 0 | 100 | 11 |
| 38 | 95 | 0 | 100 | 0 | 0 |
| 39 | 70 | 30 | 40 | 0 | 0 |
| 40 | 0 | 98 | 100 | 0 | 0 |

*Phytotoxic at 50 ppmsc, 0% Control at 25 ppmsc.
**Phytotoxic at 50 ppmsc, 0% Control at 10 ppmsc.
***Phytotoxic at 50 ppmsc, 100% Control at 25 ppmsc.

EXAMPLE 16

Residual Test for Nematicidal Activity

Test formulations of the compounds were prepared at 200 ppm by dissolving 0.05 gram of the compound to be tested in 5 ml of acetone and adding 245 ml of distilled water plus 10 drops of ethoxylated sorbitan monolaurate. For each compound, 25 ml were drenched onto 500 grams of soil in a pot for a soil concentration of 10 ppm. All experiments were conducted with four replicates each, including controls which were not treated with the active compounds. For 0, 2, and 4 week residual timings, the inoculation of nematode eggs and planting of tomato seedlings was accomplished at treatment and 2 and 4 weeks after treatment. Nineteen days after planting, the roots were examined and the percent control estimated.

The results of the testing are given in Table IV.

TABLE IV

| Cmpd. No. | Percent Control | | |
|---|---|---|---|
| | 0 Week | 2 Week | 4 Week |
| 3 | 100 | 100 | 100 |
| 11 | 100 | 99 | 99 |
| 13 | 88 | 55 | 15 |
| 14 | 100 | 100 | 99 |
| 17 | 97 | 90 | 89 |

TABLE IV-continued

| Cmpd. No. | Percent Control | | |
|---|---|---|---|
| | 0 Week | 2 Week | 4 Week |
| 22 | 100 | 63 | 97 |
| 23 | 99 | 60 | 65 |
| 24 | 100 | 100 | 89 |
| 25 | 100 | 100 | 100 |

EXAMPLE 17

Systemic Test for Rice Planthopper Activity

Test formulations of the compounds were prepared at 200 ppm by dissolving 0.01 gram of the compound to be tested in 5 ml of acetone and adding 45 ml of distilled water plus 2 drops of ethoxylated sorbitan monolaurate.

A 25 ml aliquot of each test solution was injected into the root zone of each pot with a hypodermic needle and syringe. Each pot held about 475 grams of moist soil. The resulting soil concentrations of each compound to be tested was 10 ppm. Each pot contained approximately 20 Mars variety rice seedlings, 8 days old from seed, when treated. One day after treatment, the plants were covered with a tubular cage and ten adult rice delphacids, *Sogatodes oryzicola*, were transferred into each cage. Five days after transferring, counts were made of the surviving planthoppers in each pot and the adjusted percent control was calculated using Abbott's formula.

In this test Compounds Nos. 3 and 14 gave 100% control at 10 ppmsc.

What is claimed is:

1. A compound having the structural formula

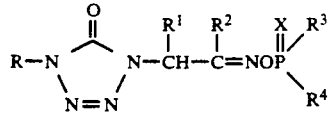

where R is lower alkyl, phenyl, substituted phenyl, naphthyl or substituted naphthyl; $R^1$ is hydrogen or $C_1$-$C_6$ alkyl; $R^2$ is $C_1$-$C_6$ alkyl or phenyl; $R^3$ is $C_1$-$C_6$ alkoxy, $C_1$-$C_6$ alkyl or $C_1$-$C_6$ alkylthio; $R^4$ is $C_1$-$C_6$ alkoxy, $C_1$-$C_6$ alkylthio, $C_1$-$C_6$ alkylamino or $C_1$-$C_6$ dialkylamino; and X is oxygen or sulfur.

2. A compound in accordance with claim 1 where R is $C_1$-$C_4$ alkyl or phenyl; $R^1$ is hydrogen or methyl; $R^2$ is $C_1$-$C_2$ alkyl or phenyl; $R^3$ is $C_1$-$C_4$ alkylthio or alkoxy; and $R^4$ is $C_1$-$C_4$ alkoxy, $C_1$-$C_4$ alkylamino alkoxy or $C_1$-$C_4$ alkylthio.

3. A compound in accordance with claim 2 wherein R is methyl; $R^1$ is hydrogen; $R^2$ is methyl or phenyl; $R^3$ is and $R^4$ is ethoxy, $C_1$-$C_4$ alkylamino or butylthio. ethoxy;

4. A compound in accordance with claim 3 wherein $R^2$ is methyl; $R^4$ is ethoxy; and X is sulfur.

5. A compound in accordance with claim 3 wherein $R^2$ is phenyl; $R^4$ is ethoxy; and X is sulfur.

6. A compound in accordance with claim 3 wherein $R^2$ is methyl; $R^4$ is sec-butylthio; and X is oxygen.

7. A composition comprising a) a pesticidally effective amount of a compound according to claim 1, and b) an agriculturally acceptable carrier.

8. A process for controlling pests comprising applying a pesticidally effective amount of a compound according to claim 1 to the locus to be protected from pests.

9. A process in accordance with claim 8 wherein said pests are soil insects, nematodes or acarids.

10. A process in accordance with claim 9 wherein said pests are nematodes.

* * * * *